(12) United States Patent
Grünberg et al.

(10) Patent No.: US 12,276,627 B2
(45) Date of Patent: Apr. 15, 2025

(54) SAMPLE HOLDER, SYSTEM, AND METHOD FOR ANALYZING ENERGETIC MATERIALS

(71) Applicants: INNOVATEC GERÄTETECHNIK GMBH, Rheinbach (DE); EXPLOTECH GMBH, Cologne (DE); HOCHSCHULE BONN-RHEIN-SIEG, Sankt Augustin (DE)

(72) Inventors: Florian Grünberg, Bonn (DE); Dirk Schulze, Bonn (DE); Gerhard Holl, Cologne (DE); Alfred Holl, Cologne (DE)

(73) Assignees: INNOVATEC GERÄTETECHNIK GMBH, Rheinbach (DE); HOCHSCHULE BONN-RHEIN-SIEG, Sankt Augustin (DE); EXPLOTECH GMBH, Siegburg (DE)

(*) Notice: Subject to any disclaimer, the term of this patent is extended or adjusted under 35 U.S.C. 154(b) by 578 days.

(21) Appl. No.: 17/592,280

(22) Filed: Feb. 3, 2022

(65) Prior Publication Data
US 2022/0252533 A1   Aug. 11, 2022

(30) Foreign Application Priority Data
Feb. 5, 2021   (DE) ............ 10 2021 102 720.9

(51) Int. Cl.
*G01N 25/48*   (2006.01)
*G01N 33/00*   (2006.01)

(52) U.S. Cl.
CPC ....... *G01N 25/486* (2013.01); *G01N 33/0016* (2013.01)

(58) Field of Classification Search
CPC ................... G01N 25/486; G01N 33/0016
See application file for complete search history.

(56) References Cited

U.S. PATENT DOCUMENTS

| | | |
|---|---|---|
| 2005/0163188 A1* | 7/2005 | Nishimura ......... G01N 25/4826 374/10 |
| 2010/0240140 A1 | 9/2010 | Fine et al. |
| 2017/0133212 A1* | 5/2017 | Mensa ............... H01J 49/0422 |
| 2018/0067067 A1 | 3/2018 | Kale et al. |

FOREIGN PATENT DOCUMENTS

| | | |
|---|---|---|
| DE | 10 2015 118 728 A1 | 5/2017 |
| WO | WO 2011/070578 A2 | 6/2011 |

* cited by examiner

*Primary Examiner* — Randy W Gibson
(74) *Attorney, Agent, or Firm* — Pauley Erickson & Swanson (57) ABSTRACT

A sample holder for a system for analyzing energetic materials, including a first holder element having a first heating element, the heating element embodied as a resistance heater and having at least one first sample region provided for accommodating a sample. A second holder element having a second heating element, the heating element embodied as a resistance heater and having at least one second sample region provided for being brought into contact with a sample. A device for connecting the holder elements so as to enclose a sample between the first sample region and the second sample region.

23 Claims, 5 Drawing Sheets

SAMPLE HOLDER, SYSTEM, AND METHOD FOR ANALYZING ENERGETIC MATERIALS

CROSS REFERENCE TO RELATED APPLICATION

German Patent Reference DE 10 2021 102 720.9, filed 5 Feb. 2021, the priority document corresponding to this invention, to which a foreign priority benefit is claimed under Title 35, United States Code, Section 119 and its entire teachings tire incorporated, by reference, into this specification.

BACKGROUND OF THE INVENTION

Field of the Invention

This invention relates to a sample holder for a system for analyzing energetic materials. It also relates to a system and a method for analyzing energetic materials.

Discussion of Related Art

Energetic materials are understood to be substances or mixtures that can release chemical energy in a very short unit without being thus dependent un the supply of oxygen or other reaction partners from the surrounding environment. Typical energetic materials are fuels or explosives.

The detection of materials, even energetic materials, by spectroscopic methods is known. Such a method, however, requires the availability of a library of reference spectra. This approach is not capable of detecting substances that have not been detected previously.

German Patent Reference DE 10 2015 118 728 A1 discloses an analysis system for a library-independent, qualitative detection of energetic materials. In this case, a sample of the material that is to be analyzed is placed into a sample chamber that can be heated from at least two sides and is then heated. Pressure sensors are able to detect an explosive reaction of the sample.

U.S. Patent Application Publication US 2018/067067 A1 discloses a microcalorimeter for testing explosives that has two heating elements for differential measurement.

U.S. Patent Application Publication US 2010/240140 A1 describes a device for analyzing energetic materials, which consists of two halves, one half being used for sample-taking and the device having a heating element.

According PCT Reference WO 2011/070578 A2, the sample-taking is performed by swiping a surface. The enclosed sample holder is then detonate by sparking between the electrodes.

In the known methods, it is disadvantageous in that the sample-taking cannot be automated well and the insertion of the sample into the sample chamber requires handling of the potentially explosive material. In addition, the thermal contact of the sample with the heating surface is insufficient so that often, an evaporation of the sample occurs instead of a detonation.

SUMMARY OF THE INVENTION

One object of this invention is to provide a sample holder, a system, and a method for analyzing energetic materials, which are particularly safe and reliable.

This object and others are attained with the subject and disclosure of this specification, the independent claims and other embodiments and advantageous designs are the subject and disclosure of the dependent claims.

According to one aspect of this invention, a sample holder for a system for analyzing energetic materials is disclosed, which includes a first holder element. The first holder element has a first heating element, which heating element is embodied as a resistance heater and has at least one first sample region provided for accommodating a sample. The sample holder also comprises a second holder element having a second heating element, which heating element is embodied as a resistance heater and has at least one second sample region provided for being brought into contact with a sample. The sample holder also includes a device for connecting the holder elements so as to enclose a sample between the first sample region and the second sample region.

The sample holder has one advantage that by enclosing the sample between the two sample regions, the sample is fully in contact with a heating element and can be heated during the entire analysis.

In addition, constructing the sample holder of at least two holder elements enables an automated sample collection. Specifically, the sample does not have to be taken with a separate device and then placed onto the sample region, and instead at least one of the holder elements is already suitably embodied as a sample-taking device. Consequently, this holder element can be advanced toward the material to be analyzed and brought into contact with it so that a sample of the material remains on the sample region. This sample is enclosed between the two sample regions when the two holder elements are subsequently connected to each other.

In this case, the enclosing of the sample can be embodied as a very tight enclosure, which enables a clear pressure signal. With a tight enclosure of this kind, the sample regions are pressed directly against each other so that there is no measurable dead volume remaining. As a result, the sample holder can also be very compactly embodied.

According to one embodiment, the first and/or second sample region has an increased surface roughness in comparison to the remaining surface of the first and/or second heating element. In this ease, the increased surface roughness can be produced, for example, by of structures such as nubs or pores and/or an adhesive coating. The increased surface roughness facilitates the taking and adhering of a sample in the sample region and thus the use of the holder element as a sample-taking device.

According to one embodiment, the first and/or second sample region protrudes relative to other regions of the first and/or second heating element. In other words, the relevant holder element has a convex surface curvature in the sample region.

With the sample region embodied in such a way, it is particularly simple to bring it into contact with the material to be analyzed, without requiring the material to be handled with other devices. This enables a particularly safe sample-taking and analysis.

According to one embodiment, the first heating element extends along a first longitudinal axis and the second heating element extends along a second longitudinal axis, the longitudinal axes crossing when the holder elements are connected to each other by the device for connecting the holder elements. In particular, the longitudinal axes can cross at a right angle. Such an arrangement achieves the fact that the temperature of the heating elements is particularly high in the crossing region.

In order to particularly increase the temperature in the region of the enclosed sample, the first and/or second sample region of the heating elements can have a higher electrical resistance than other sections of the first and/or second heating element. This achieves a particularly intense heating of the heating element in the sample region. The particularly high electrical resistance can, for example, be achieved by a reduction of the thickness of the heating element, by a reduction of the width, or for example through the provision of openings.

According to one embodiment, each heating element has two contacting holes. A contacting pin can be inserted through each of these holes when the sample holder is inserted into a socket provided for it in the system for analyzing energetic materials. The holes can be embodied in such a way that their edges clean the surfaces of the contact pins when the contact pins are inserted through them. This can in particular be achieved by virtue of the fact that regions of the edges are supported in resilient fashion against the respective contact pin and slide tightly along it when the contact pin is guided through the contacting hole.

The first holder element or the second holder element can have a window that is transparent for electromagnetic radiation, for example infrared radiation, in which a region of at least one heating element is exposed. For example, a back side of the second sample region can be exposed in the window. This has one advantage that a particularly simple and safe temperature measurement can take place in the sample region.

The first holder element and the second holder element can each have a plastic body on which the first heating element and second heating element are positioned. The embodiment by a plastic body has one advantage that the entire sample holder can be embodied as a disposable or throw-away article intended for a single use. Suitable materials are in particular plastics, which, even at an elevated temperature, do not release any volatile substances that disrupt the analysis.

According to one embodiment, a hollow space is provided in the first holder element adjacent to the sample region of the heating element. Substances that are generated when the sample is heated are released into the hollow space. For the analysis of these substances, the hollow space is connected to an outlet of the sample holder, which in turn can be connected to a cavity of a system for analyzing energetic materials, and substances contained in the cavity can be accessed for an analysis, for example by gas sensors. In addition, pressure sensors can be provided for monitoring the pressure in the cavity. In order to prevent impurities in the sample holder from penetrating into the cavity, a filter can be provided at the outlet of the sample holder.

According to another aspect of this invention, a system for analyzing energetic materials is provided with or has a socket for the above-described sample holder, and the system also has contact pins for the production of an electrical contact of the heating elements of the sample holder when the latter is positioned in the socket and has at least one pressure sensor for detecting a pressure signal of a sample.

In addition, the system can also have gas sensors for analyzing gases that are generated when a sample is heated as well as a device for temperature measurement by infrared radiation.

The system enables a quick and reliable analysis of even unknown materials and a largely automatable and thus less dangerous sample-taking and analysis.

According to one embodiment, the system also has a device for generating a vacuum in a measurement region of the pressure sensor. The device can, for example be a fan or a pump that extracts gas from the measurement region of the pressure sensor.

This embodiment has various advantages. On the one hand, the device for generating a vacuum offers an option to extract gases after an analytical procedure and thus to flush out the system. On the other hand, when a vacuum is generated before the measurement, the measurement is performed against a low background so that the pressure signal is particularly clear.

According to another aspect of this invention, a method for analyzing energetic materials is disclosed, which comprises the taking of a sample of a material by a first heating element embodied as a resistance heater by virtue of a sample region of the heating element being brought into contact with the material as well as the enclosing of the sample between the first heating element and a second heating element that is likewise embodied as a resistance heater. The method also includes the heating of the sample through the supply of power to the heating elements and the acquisition of a pressure signal by at least one pressure sensor.

According to one embodiment, the method also comprises the generation of a vacuum in a measurement region of the pressure sensor before the heating of the sample.

After the analysis has been carried out, a vacuum can be generated again in order to extract released gases from the system and to flush out the system.

BRIEF DESCRIPTION OF THE DRAWINGS

Embodiments of this invention will be explained in greater detail below in view of schematic figures, wherein.

DETAILED DESCRIPTION OF THE INVENTION

Figure 1:
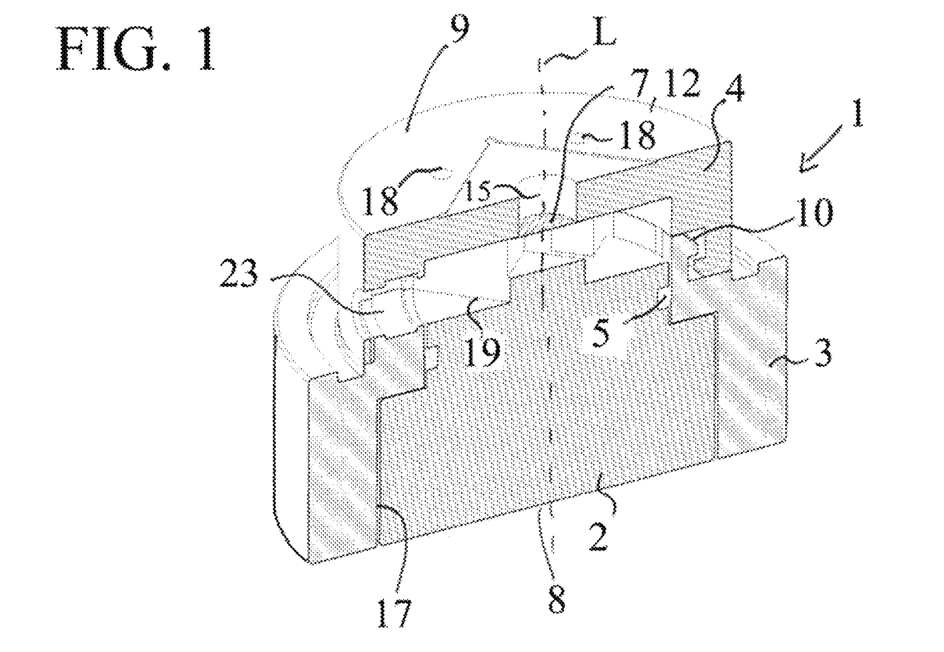
FIG. 1 shows a longitudinal section taken through a sample holder according to a first embodiment of this invention.
Figure 2:
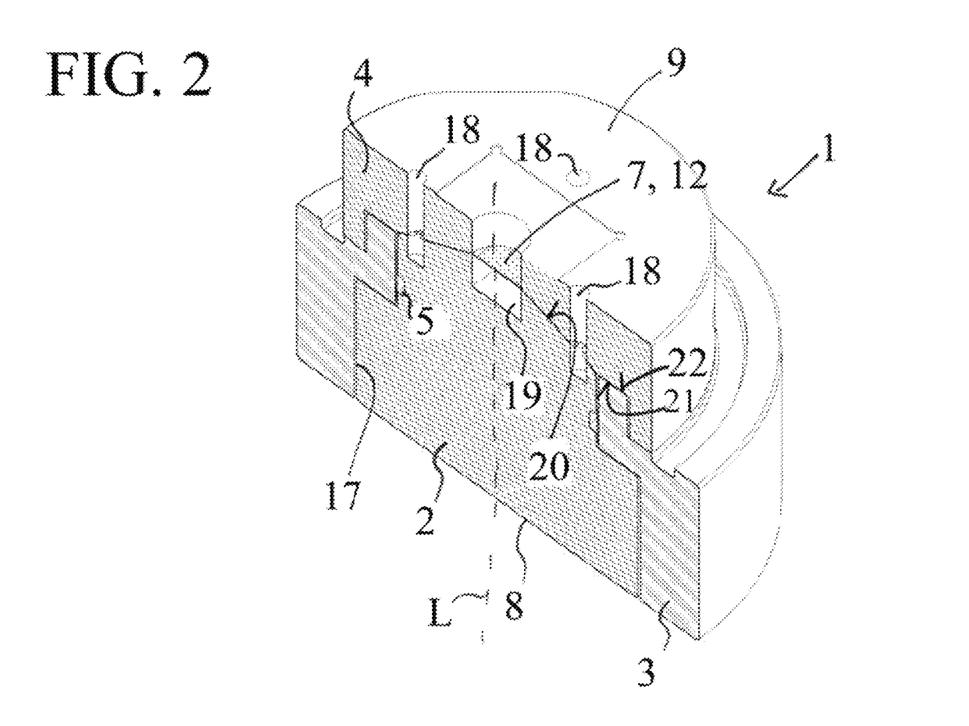
FIG. 2 shows a longitudinal section taken through the sample holder that is rotated by 90° relative to FIG. 1.

FIGS. 1 and 2 show sections along the longitudinal axis L through a sample holder 1 for a system for analyzing energetic materials according to one embodiment of this invention.

In the embodiment shown, the sample holder 1 comprises two subassemblies, which can be connected to each other. The first subassembly comprises a first holder element 2 that is preferably made of plastic, for example polyamide. The second subassembly comprises a second holder element 3 and a third holder element 4, which are likewise preferably made of plastic, for example polyamide, and are connected to each other by a snap connection 10. The second subassembly has a recess 17 into which the first holder element 2 can be inserted. Between the two subassemblies are positioned the heating elements 6, 7 that are shown in greater detail in FIGS. 3-5, and only the second heating element 7 is visible in FIGS. 1 and 2.

Figure 3:
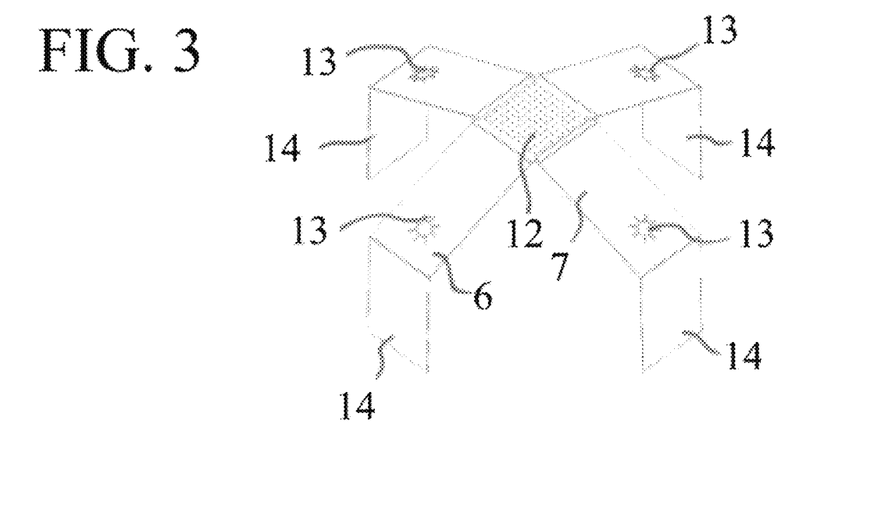
FIG. 3 shows two heating elements of the sample holder, in a perspective view.
Figure 4:
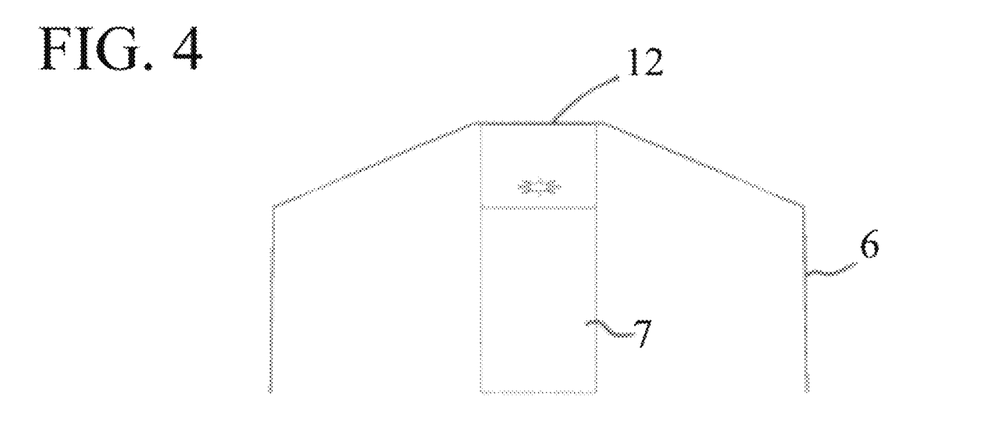
FIG. 4 shows the heating elements according to FIG. 3, in a side view.
Figure 5:
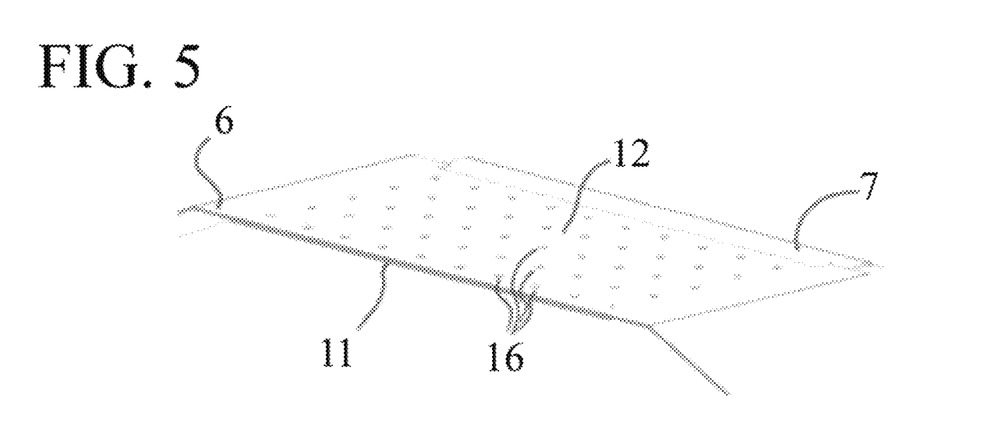
FIG. 5 shows a detail from FIG. 3.

As shown in FIGS. 3 to 5, the heating elements 6, 7 each comprise a metal strip, for example made of a constantan foil, with a centrally located sample region. In addition, each heating element 6, 7 has two contacting holes 13 for the production of an electrical contact. In the embodiment shown here, each heating element 6, 7 also has fastening sections 14, which are each provided at the two ends of the heating elements 6, 7 and in the installed state of the heating elements 6, 7, are bent at an angle. The heating elements 6, 7 are fastened to the holder elements 2, 3, 4 by the fastening sections 14.

In order to fasten the first heating element 6 to the first holder element 2, the second holder element 2 has a circumferential groove 5 into which an O-ring can be inserted. In order to prepare the first holder element 2 for the sample-taking, the first heating element 6 is placed onto an upper contour 20 of the first holder element 2 and the fastening sections 14 are clamped by the O-ring that is inserted into the groove 5. The first heating element 6 is thus affixed to the first holder element 2 in a simple way.

In order to prepare the second subassembly, which consists of or includes the second holder element 3 and the third holder element 4, for the sample-taking, and the analysis, the second heating element 7 is clamped between a lower contour 21 of the third holder element 4 and an upper contour 22 of the second holder element 3. If the first holder element 2 is then inserted into the recess 17 in the second subassembly, then the sample regions 11, 12 of the two heating elements 6, 7 rest against each other.

In the embodiment shown, the sample holder 1 has three holder elements 2, 3, and 4. It is also possible, however, to provide only two holder elements if the second heating element 7 is fastened in a different way.

In the third holder element 4, a window 15 that is transparent for infrared radiation is provided, behind which the second sample region 12 is exposed for a temperature measurement.

The sample regions 11, 12 of the heating elements 6, 7 have an increased surface roughness, for example in the form of nubs or pores, in order to improve an adhesion of a sample. This is not shown in the figures. In the sample regions 11, 12, the heating elements 6, 7 also have a number of through holes 16, which can, for example, be produced by laser drilling or punching. The through holes 16 serve to increase the electrical resistance of the heating elements 6, 7 in the sample regions 11, 12.

For the sample-taking and analysis, the following procedure is performed. The first holder element 2 that is provided with the first heating element 6 is advanced toward the material that is to be analyzed and is brought into contact with it. This is particularly facilitated because the upper contour 20 of the first holder element 2 with the first sample region 11 is embodied as convex. As a result, a sample of the material adheres in the first sample region 11 of the first heating element 6.

The first holder element 2 that is provided with the sample in this way is inserted into the recess 17 in the second holder element 3 and is pressed far enough into it that the surfaces of the first holder element 2 and the second holder element 3 are flush on a first side 8 of the sample holder 1. In this position, the first holder element 2 is frictionally connected to the second holder element 3 by the O-ring that is inserted into the groove 5. The O-ring that is inserted into the groove 5, together with the dimensions of the recess 17 and of the first holder element 2, thus constitutes or forms a device for connecting the holder elements 2, 3 so as to enclose the sample between the first sample region 11 and the second sample region 12. The sample regions 11, 12 of the heating elements 6, 7 therefore rest against each other and the sample is thus tightly enclosed between the heating elements 6, 7.

The sample holder 1 is then inserted into a socket provided for it in a system for analyzing energetic materials, which is not shown. In the course of this, contact pins of the system push into holes 18 of the third holder element 4, which expose a second side 9 of the sample holder 1, and come into contact with the heating elements 6, 7 in the region of or near the contacting holes 13. Because the contacting holes 13 have a smaller diameter than the holes 18, but have slit rims, as is also visible in FIG. 3, the material of the heating elements 6, 7 in the rim region of the contacting holes 13 can bend and rest tightly against the contact pins. This also enables a cleaning of the contact pins as they are being inserted and pulled out. The heating elements 6, 7 are supplied with power via the contact pins and the electrical contact in the region of or near the contacting holes 13. As a result, the temperature increases and because of the overlapping of the heating elements 6, 7 and because of the particularly high electrical resistance in the sample regions 11, 12, the temperature reaches a maximum in this region.

If the sample that is to be analyzed is an energetic material, then if a material-dependent temperature threshold is exceeded, this material is detonated and a pressure sensor of the system registers a corresponding pressure increase.

With a hollow space 19 positioned under the sample regions 11, 12 between the first holder element 2 and the third holder element 4 with an outlet 23 into which a filter can be inserted, the sample or more precisely, its reaction products can be accessed for an analysis. For this purpose, the system can in particular have gas sensors.

Figure 6:
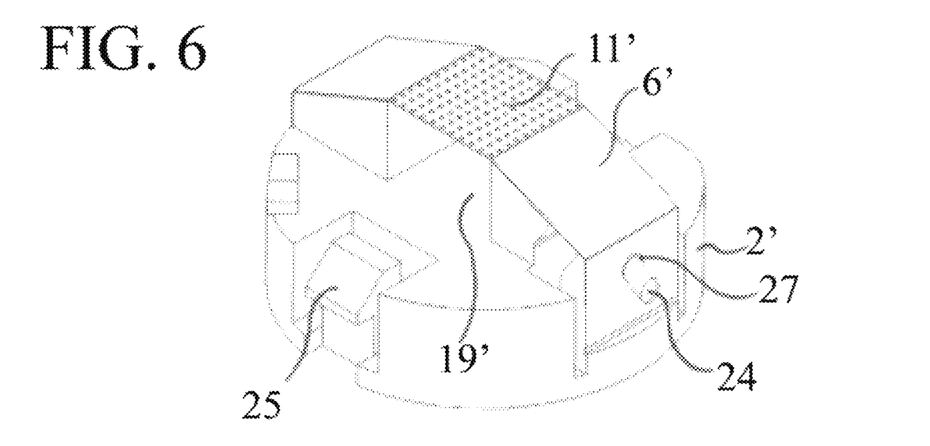
FIG. 6 shows a perspective view of a first holder element for a sample holder according to a second embodiment of this invention.
Figure 7:
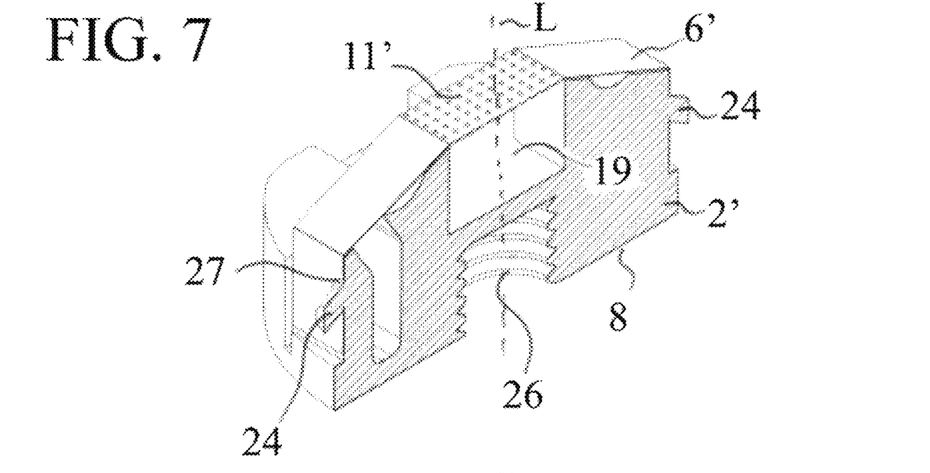
FIG. 7 shows a longitudinal section taken through the holder element according to FIG. 6.
Figure 8:
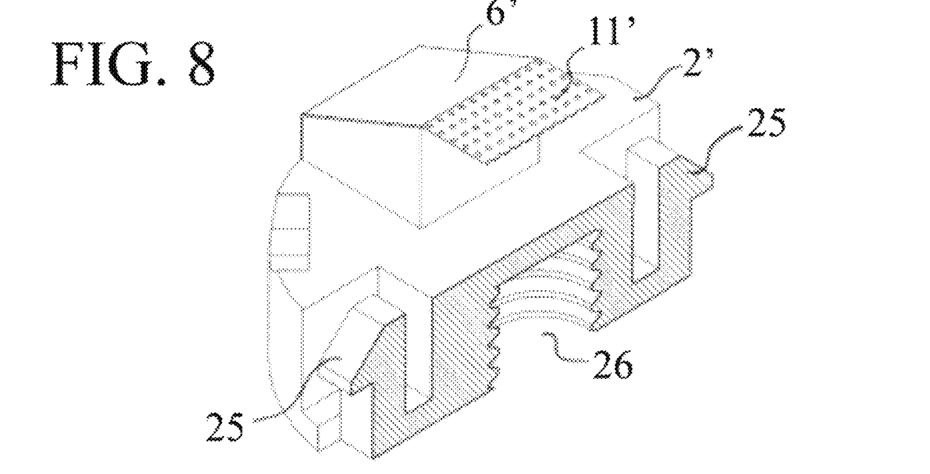
FIG. 8 shows a longitudinal section that is rotated by 90 degrees relative to FIG. 7.
Figure 9:
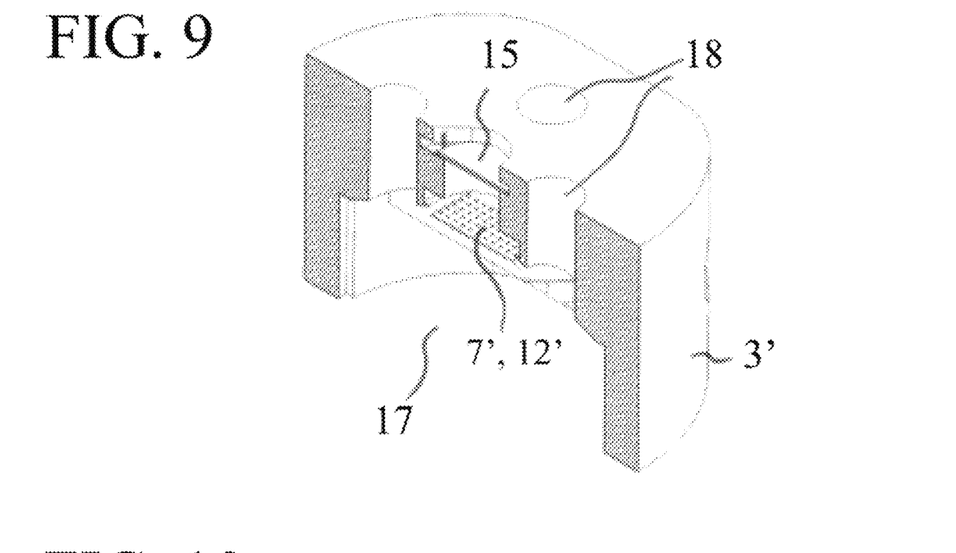
FIG. 9 shows a longitudinal section taken through a second holder element for the sample holder according to the second embodiment of this invention.
Figure 10:
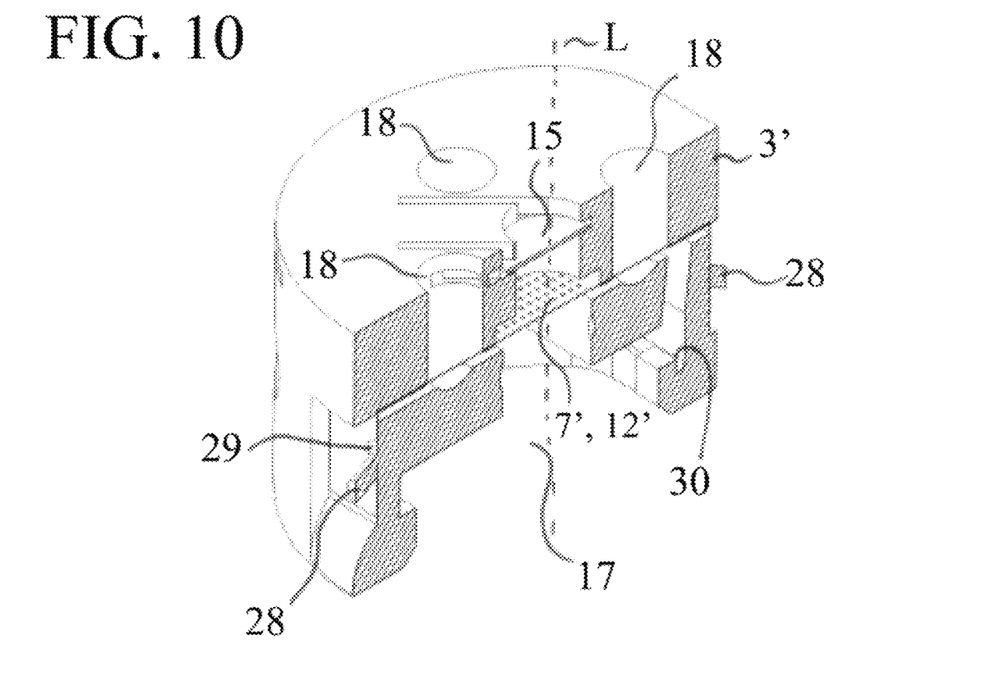
FIG. 10 shows a longitudinal section that is rotated by 90 degrees relative to FIG. 9.
Figure 11:
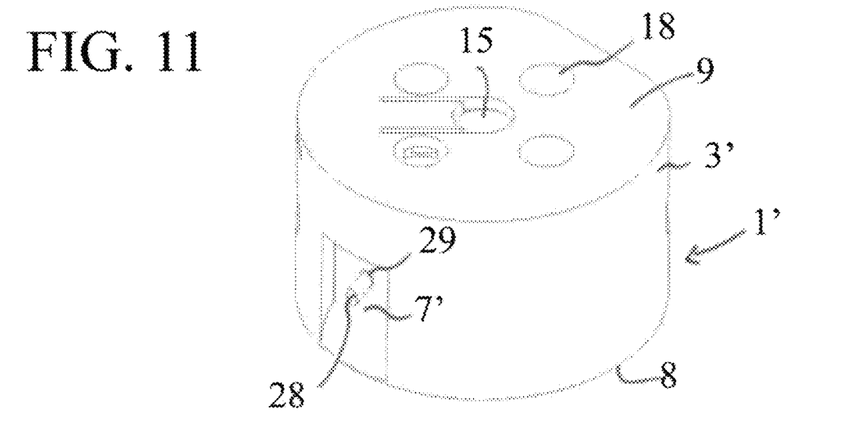
FIG. 11 shows a perspective view of the sample holder according to the second embodiment of this invention.
Figure 12:
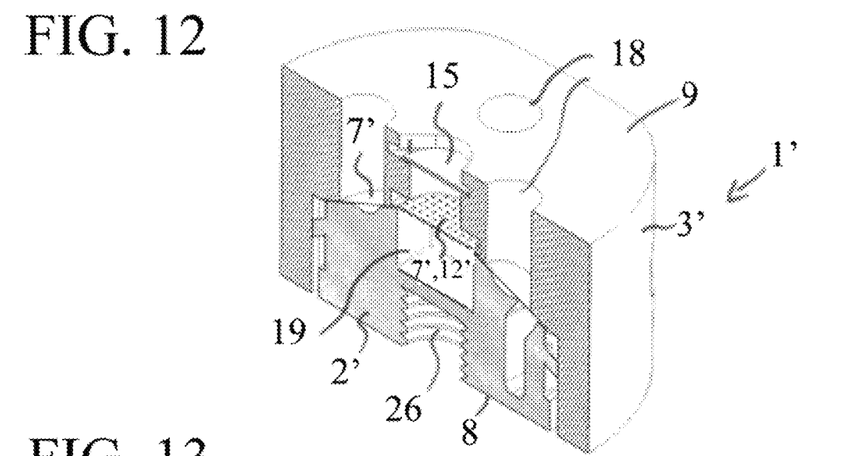
FIG. 12 shows a longitudinal section taken through the sample holder according to FIG. 11.
Figure 13:
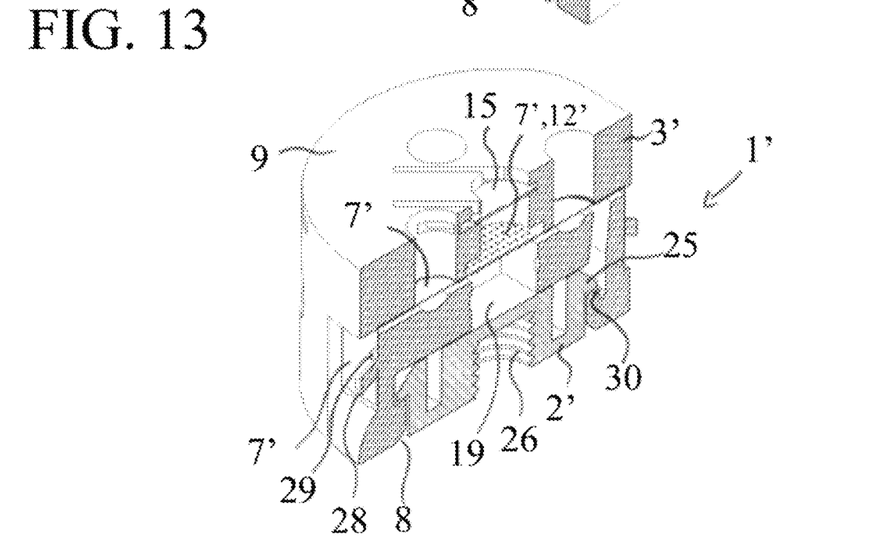
FIG. 13 shows a longitudinal section taken through the sample holder that is rotated by 90 degrees relative to FIG. 12.

FIGS. 6 to 13 show a second embodiment of a sample holder. In this case, FIGS. 6 to 8 show different views of a first holder element 2', FIGS. 9 and 10 show two different views of a second holder element 3' and FIGS. 11 to 13 show different views of the entire sample holder 1', which comprises the first holder element 2' and the second holder element 3'.

The first holder element 2' shown in FIGS. 6 to 8 differs from the first embodiment shown in FIGS. 1 and 2, mainly in that the heating element 6' is fastened to the first holder element 2' in a different way. According to the second embodiment, the first holder element 2' has projections 24 on two opposing sides, which protrude from a side surface of the holder element 2'. In each of its two end regions, the heating element 6' has a respective hole 27 through which the projections 24 can be guided. The projections 24 can be embodied as resilient in order to facilitate the fastening of the heating element 6'. In addition, the heating element 6' can be made of a somewhat flexible material, for example a film made of constantan. In order to be mounted on the holder element 2', the heating element 6' can first be fastened on one side in that one of the projections 24 is guided through one of the holes 27. Then, the heating element 6' is stretched toward the opposite side of the holder element 2' and the second projection 24 is guided through the corresponding hole 27.

In addition, according to the second embodiment, the first holder element 2' has snap hooks 25 on two opposing sides, which snap onto a projection of the second holder element, as shown in FIGS. 12 and 13.

In FIGS. 7 and 8, which each show sectional views of the first holder element 2' that are rotated by 90° relative to each other, a threaded bore 26 is also shown, which extends from the first side 8 in the first holder element 2'. The threaded bore 26 makes it possible to fasten a threaded rod, which is not shown in the figures, to the first holder element 2 in order to be able to perform the sample-taking in the least risky manner. The first holder element 2', which can have a diameter of a few centimeters, can then be inserted with the aid of the threaded rod into a container that contains an unknown substance that is to be tested. Then the first holder element 2', likewise with the aid of the threaded rod or after the removal of the threaded rod, can be inserted into the recess provided for it in the second holder element.

The second holder element 3' according to the second embodiment is shown in two sectional depictions in FIGS. 9 and 10, which are rotated by 90° relative to each other. The second holder element 3' differs from the one shown in FIGS. 1 and 2, mainly in the way in which the second heating element 7' is fastened, which in this case as well is carried out so that projections 28 on opposing sides of the second holder element 3' are guided through holes 29 at two ends of the second heating element 7'. The second heating element 7' is fastened to the second holder element 3' analogously to the way in which the first heating element 6' is fastened to the first holder element 2'.

The second holder element 3', which according to the second embodiment, can be embodied of one piece by contrast with the first embodiment, also has a shoulder 30, which surrounds or at least partially surrounds a recess 17 and on which the snap hooks 25 of the first holder element 2' are supported when the first holder element 2' is inserted far enough into the recess 17. In this position, the sample regions 11', 12' of the heating elements 6', 7' then rest against each other and enclose the sample between themselves.

This position is shown in FIGS. 11 to 13, which show the entire sample holder 1' according to the second embodiment. In this position, the first holder element 2' has been completely inserted into the recess 17 of the second holder element 3' and is snap-connected to it. In the holes 18, regions of the heating elements 6', 7' are exposed for the production of an electrical contact for purposes of the resistance heating. Below the sample regions 11', 12' is the hollow space 19 via which the sample or more precisely its reaction products can be accessed for an analysis.

Through a window 15 on a second side 9 of the sample holder 1', the sample region 12' of the second heating element 7' can be accessed for an infrared temperature measurement, as described in connection with the first embodiment.

While in the foregoing specification this invention has been described in relation to certain preferred embodiments, and many details are set forth for purpose of illustration, it will be apparent to those skilled in the art that this invention is susceptible to additional embodiments and that certain of the details described in this specification and in the claims can be varied considerably without departing from the basic principles of this invention.

What is claimed is:

1. A sample holder (1) for a system for analyzing energetic materials, comprising:
    a first holder element (2) having a first heating element (6), the heating element (6) embodied as a resistance heater and having at least one first sample region (11) provided for accommodating a sample;
    a second holder element (3, 4) having a second heating element (7), the second heating element (7) being embodied as a resistance heater and having at least one second sample region (12) for being brought into contact with a sample; and
    a device for connecting the holder elements (2, 3, 4) so as to enclose a sample between the first sample region (11) and the second sample region (12).

2. The sample holder (1) according to claim 1, wherein the first and/or the second sample region (11, 12) has an increased surface roughness in comparison to the remaining surface of the first and/or second heating element (6, 7).

3. The sample holder (1) according to claim 2, wherein the first and/or the second sample region (11, 12) protrudes relative to other regions of the first and/or second heating element (6, 7).

4. The sample holder (1) according to claim 3, wherein the first heating element (6) extends along a first longitudinal axis and the second heating element (7) extends along a second longitudinal axis, the longitudinal axes crossing when the holder elements (2, 3, 4) are connected to each other by the device for connecting the holder elements (2, 3, 4).

5. The sample holder (1) according to claim 4, wherein the first and/or the second sample region (11, 12) has a higher electrical resistance than other sections of the first and/or second heating element (6, 7).

6. The sample holder (1) according to claim 5, wherein each heating element (6, 7) has two contacting holes (13).

7. The sample holder (1) according to claim 6, wherein at least one holder element (2, 3, 4) has a window (15) that is transparent for electromagnetic radiation, in which a region of at least one heating element (6, 7) is exposed.

8. The sample holder (1) according to claim 7, wherein the first holder element (2) and the second holder element (3, 4) each have a plastic body on which the first heating element (6) and the second heating element (7) are positioned.

9. The sample holder (1) according to claim 8, wherein a hollow space (19) is provided in the first holder element (2) adjacent to the sample region (11) of the heating element (6).

10. A system for analyzing energetic materials with a socket for a sample holder (1) according to claim 9, wherein the system further comprises contact pins for the production of an electrical contact of the heating elements (6, 7) of the sample holder (1) when the latter is positioned in the socket, and at least one pressure sensor for detecting a pressure signal of a sample.

11. The system according to claim 10, wherein the system has gas sensors for analyzing gases that are generated when a sample is heated.

12. The system according to claim 11, wherein the system has a device for generating a vacuum in a measurement region of the pressure sensor.

13. A method for analyzing energetic materials, comprising:
    taking a sample of a material with a first heating element (6) embodied as a resistance heater by virtue of a sample region (11) of the heating element (6) being brought into contact with the material;

enclosing the sample between the first heating element (6) and a second heating element (7) that is embodied as a resistance heater;

heating of the sample through the supply of power to the heating elements (6, 7), before the heating of the sample, a vacuum is generated in a measurement region of the pressure sensor; and acquisition of a pressure signal by at least one pressure sensor.

14. The sample holder (1) according to claim 1, wherein the first and/or the second sample region (11, 12) protrudes relative to other regions of the first and/or second heating element (6, 7).

15. The sample holder (1) according to claim 1, wherein the first heating element (6) extends along a first longitudinal axis and the second heating element (7) extends along a second longitudinal axis, the longitudinal axes crossing when the holder elements (2, 3, 4) are connected to each other by the device for connecting the holder elements (2, 3, 4).

16. The sample holder (1) according to claim 1, wherein the first and/or the second sample region (11, 12) has a higher electrical resistance than other sections of the first and/or second heating element (6, 7).

17. The sample holder (1) according to claim 1, wherein each heating element (6, 7) has two contacting holes (13).

18. The sample holder (1) according to claim 1, wherein at least one holder element (2, 3, 4) has a window (15) that is transparent for electromagnetic radiation, in which a region of at least one heating element (6, 7) is exposed.

19. The sample holder (1) according to claim 1, wherein the first holder element (2) and the second holder element (3, 4) each have a plastic body on which the first heating element (6) and the second heating element (7) are positioned.

20. The sample holder (1) according to claim 1, wherein a hollow space (19) is provided in the first holder element (2) adjacent to the sample region (11) of the heating element (6).

21. A system for analyzing energetic materials with a socket for a sample holder (1) according to claim 1, wherein the system further comprises contact pins for the production of an electrical contact of the heating elements (6, 7) of the sample holder (1) when the latter is positioned in the socket, and at least one pressure sensor for detecting a pressure signal of a sample.

22. The system according to claim 1, wherein the system has gas sensors for analyzing gases that are generated when a sample is heated.

23. The system according to claim 10, wherein the system has a device for generating a vacuum in a measurement region of the pressure sensor.

* * * * *